United States Patent [19]
Reno et al.

[11] Patent Number: 4,877,868
[45] Date of Patent: Oct. 31, 1989

[54] RADIONUCLIDE ANTIBODY COUPLING

[75] Inventors: John M. Reno; Becky J. Bottino, both of Lynnwood; D. Scott Wilbur, Edmonds, all of Wash.

[73] Assignee: NeoRx Corporation, Seattle, Wash.

[21] Appl. No.: 838,992

[22] Filed: Mar. 12, 1986

[51] Int. Cl.$^4$ ............................................... C07K 3/00
[52] U.S. Cl. ................................... 530/390; 530/389; 530/402; 424/1.1; 424/DIG. 6; 435/810; 436/547; 436/548; 534/10
[58] Field of Search ................ 436/547, 548; 530/389, 530/390, 402; 424/DIG. 6, 1.1; 435/810; 534/10

[56] References Cited

U.S. PATENT DOCUMENTS

| | | |
|---|---|---|
| 2,662,079 | 12/1953 | Friedheim ................ 424/DIG. 6 |
| 4,022,887 | 5/1977 | Huber et al. . |
| 4,027,005 | 5/1977 | Adler et al. . |
| 4,031,198 | 6/1977 | Jackson et al. . |
| 4,042,677 | 8/1977 | Molinski et al. . |
| 4,057,615 | 11/1977 | Bardy et al. . |
| 4,057,617 | 11/1977 | Abramovici et al. . |
| 4,059,571 | 11/1977 | Tomibe et al. . |
| 4,235,869 | 11/1980 | Schwarzberg . |
| 4,272,506 | 6/1981 | Schwarzberg . |
| 4,293,537 | 10/1981 | Wong . |
| 4,305,922 | 12/1981 | Rhodes . |
| 4,323,546 | 4/1982 | Crockford et al. . |
| 4,340,535 | 7/1982 | Voisin et al. . |
| 4,347,179 | 8/1982 | Ono et al. . |
| 4,401,647 | 8/1983 | Krohn et al. . |
| 4,418,052 | 11/1983 | Wong . |
| 4,421,735 | 12/1983 | Haber et al. . |
| 4,424,200 | 1/1984 | Crockford et al. . |
| 4,454,106 | 6/1984 | Gansow et al. . |
| 4,470,925 | 9/1984 | Auditore-Hargreaves ......... 530/390 |
| 4,472,371 | 9/1984 | Burchiel et al. . |
| 4,472,509 | 9/1984 | Gansow et al. . |
| 4,478,815 | 10/1984 | Burchiel et al. . |
| 4,636,380 | 1/1987 | Wong . |
| 4,647,655 | 3/1987 | Axen et al. . |
| 4,652,440 | 3/1987 | Paik et al. . |
| 4,659,839 | 4/1987 | Nicolotti et al. . |
| 4,668,503 | 5/1987 | Hnatowich . |

FOREIGN PATENT DOCUMENTS

| | | |
|---|---|---|
| EP 0005638 | 11/1979 | European Pat. Off. . |
| EP 0135160 | 3/1985 | European Pat. Off. . |
| EP 0188256 | 7/1986 | European Pat. Off. . |
| 2109407 | 6/1983 | United Kingdom ................ 436/548 |
| WO 87/04164 | 7/1987 | World Int. Prop. O. . |

OTHER PUBLICATIONS

Stark, G. R., J. Biol. Chem., vol. 239, No. 5, (1964), pp. 1411–1414.

J. Steigman et al., The Importance of the Protein Sulfhydryl Group in HSA Labeling with Technetium-99m, J. Nucl. Med. 16:573 (abstract) (1975).

W. A. Pettit et al., Improved Protein Labeling by Stannous Tartrate Reduction of Pertechnetate, J. Nucl. Med. 21:59–62 (1980).

Primary Examiner—Robert J. Warden
Assistant Examiner—Stephen C. Wieder
Attorney, Agent, or Firm—NeoRx Corporation

[57] ABSTRACT

Metal radionuclide labeled proteinaceous substances which contain, in their native states, disulfide (cysteine) linkages, which find use in diagnosis and treatment of a variety of pathologic conditions. The radionuclide labeled proteinaceous substances of the present invention are formed by the treatment of the proteinaceous substance of interest with a disulfide reducing agent, followed by reaction of the reduced proteinaceous substance ("H-treated product") with a suitable radionuclide species containing, for example, $^{99m}$Tc, $^{186}$Re and $^{188}$Re, or $^{67}$Cu. It has been found that the H-treated products, e.g., antibodies, react specifically with radionuclide species to form stable radionuclide labeled antibodies or other radiolabeled products. The H-treated products may be stabilized or modified in a variety of ways prior to and subsequent to complexation with the metal radionuclide.

25 Claims, No Drawings

RADIONUCLIDE ANTIBODY COUPLING

BACKGROUND OF THE INVENTION

1. Field of the Invention

This invention relates to radiolabeled proteinaceous substances, methods for making the same, and their use as diagnostic and therapeutic agents.

Radiolabeled compounds are important tools in medical diagnosis and treatment. Such compounds are employed in a variety of techniques, including the diagnosis of deep venous thrombi, the study of lymph node pathology, and the detection, staging, and treatment of neoplasms. A number of these compounds employ metal radionuclides, such as technetium-99m. When employing radionuclides for in vivo administration, it is desirable that the radionuclide localize in a target organ or lesion, e.g., cancer site. Therefore, radionuclides are usually formulated to provide preferential binding to or absorption by the particular organ or tissue. There is considerable interest in being able to accurately direct a radionuclide to a preselected site to reduce background radiation directed to surrounding or distant tissue, reduce the dosage, minimize background for in vivo imaging, and to minimize undesirable side effects. Toward this end, methods involving specific ligands or receptors to which the radionuclide may be conjugated are of interest.

Known radiolabeled compounds and other preparations frequently suffer from one or more distinct disadvantages. For example, in such preparations, the linkage between the radionuclide and the proteinaceous substance of interest may be non-specific and/or unstable, resulting in dissociation of the preparation which, in turn, leads to an increase in background radiation, limits the diagnostic utility of the preparation, and increases the radiation dose to non-targeted sites, limiting the therapeutic efficacy.

Derivatives of proteinaceous substances with protein-chelate conjugates are more stable. However, the preparation of such protein-chelate derivatives may require that the proteinaceous substance be subjected to relatively harsh conditions, e.g., organic solvents and extremes of pH and temperature, which may result in partial denaturation. Additionally, the presence of radionuclide chelates can severely alter the biological activity of particular proteinaceous substances. For example, antibodies covalently labeled with a metal radionuclide via a chelating ligand may be of diminished immunoreactivity which, in turn, diminishes the specificity of their interaction with tissues. Also, proteins subjected to some chelate conjugation methods are prone to denaturation/aggregation; such effects can increase the rates at which such proteins are cleared from the circulation, and therefore decrease the quantity of radionuclide available for imaging or therapy. Furthermore, some proteinaceous substances which are radiolabeled utilizing chelate conjugates may induce an immune response in a patient making any further use of the labeled protein hazardous.

2. Description of the Relevant Literature

References of interest include Steigman, et al., 16 *J. Nucl. Med.* 573 (1975) (abstract); Pettit, et al., 21 *J. Nucl. Med.* 59 (1980); and U.S. Pat. Nos. 4,424,200; 4,421,735; 4,323,546; 4,293,537; and 4,057,617.

SUMMARY OF THE INVENTION

Metal radionuclide labeled proteinaceous substances are provided which contain, in their native states, disulfide (cystine) linkages, which find use in diagnosis and treatment of a variety of pathologic conditions. Specifically, chelated metal radionuclide conjugates of proteinaceous substances are employed for the diagnosis of conditions, including lymph node pathology and deep venous thrombi, and the detection and staging of neoplasms. Radionuclide labeled proteins, particularly immunoglobulins, are employed for radio therapy of tumors.

The radionuclide labeled proteinaceous substances of the present invention are formed by the treatment of the proteinaceous substance of interest with a disulfide reducing agent, followed by reaction of the reduced proteinaceous substance ("H-treated product") with a suitable radionuclide species containing, for example, $^{99m}$Tc, $^{186}$Re and $^{188}$Re, or $^{67}$Cu. It has been found that the H-treated products, e.g., antibodies, react specifically with radionuclide species to form stable radionuclide labeled antibodies or other radiolabeled products. The H-treated products may be stabilized or modified in a variety of ways prior to and subsequent to complexation with the metal radionuclide.

DESCRIPTION OF THE SPECIFIC EMBODIMENTS

Improved methods and compositions are provided related to metal radionuclide labeled proteinaceous substances, as well as the use of the radiolabeled proteinaceous substances (radiolabeled products) for radioimaging and radiotherapy. Stable intermediate products formed in the processes for producing the radiolabeled products are also provided; such intermediate products are useful where it is desired to complete preparation of the radiolabeled products, except for the radiolabeling step, well prior to administration so that only the radiolabeling need be performed immediately prior to administration.

The metal radionuclide-labeled proteinaceous substances will be formed from a selected proteinaceous substance, treatment of the selected proteinaceous substance with a disulfide reducing agent, and thereafter radiolabeled with a radionuclide.

The proteinaceous substance will be a protein, polypeptide, glycoprotein, proteoglycan, lipoprotein, or the like. Of particular interest are immunoglobulins (antibodies), either polyclonal or monoclonal antibodies, or specific binding fragments thereof. Proteinaceous substances will usually be of at least 1,000 MW, more usually at least about 2,000 MW, generally less than about 1.6 MDal, more usually less than about 800 KDal. The proteinaceous substances will be characterized by having at least one accessible disulfide linkage. By "accessible," is meant that, upon reduction, the thiol groups are available for bonding with the metal radionuclide. This may determined empirically.

A variety of metals may be employed as the radionuclide. These metals include copper, e.g., $^{67}$Cu, technetium, e.g., $^{99m}$Tc; rhenium, e.g., $^{186}$Re and $^{188}$Re; these will generally be reactive with the H-treated products as ions, e.g., $^{67}$Cu$^{2+}$, $^{99m}$Tc=O$^{3+}$, $^{186,188}$Re=O$_2$$^{3+}$, when reacted with the H-treated proteinaceous substances.

The proteinaceous substances may vary widely, depending upon the nature of the use of the radionuclide.

Thus, the compounds may be ligands or receptors. Ligands may include such a variety of compounds as hormones, lymphokines, growth factors, etc., particularly compounds binding to surface membrane receptors, where the complex may remain bound to the surface or become endocytosed. Among receptors are surface membrane receptors, antibodies, enzymes, naturally occurring receptors, lectins, and the like. Of particular interest are immunoglobulins or their equivalent, which may involve Fab fragments, F(ab')$_2$, F$_v$, T-cell receptors, etc.

Generally, the selected proteinaceous substance will be treated with a stoichiometric excess of a disulfide reducing agent such as dithiothreitol (DTT) in an aqueous medium, generally of about pH 5–8, typically 6–7, and the reaction allowed to proceed for a sufficient time for all of the selected proteinaceous substances to react with the reducing agent. Usually, the time will be less than about six hours and more than about 15 minutes, with temperatures ranging from about 0° to 50° C., usually not exceeding about 40° C., and preferably about 25° C. The particular conditions will be selected in accordance with the particular proteinaceous substance, the pH, and the like.

Although DTT is the preferred reagent for treatment of the proteinaceous substances, other reducing agents, which may contain a mercaptan group or a pair of mercaptan groups, may find use, e.g. sodium borohydride, sodium phosphorothioate, dithioerythritol (DTE), 2-mercaptoethanol, cysteine, N-acetyl cysteine, and glutathione.

After reduction of the disulfide(s) of the proteinaceous substance, the reducing agent will normally be removed to prevent complexation with the radionuclide and to avoid any adverse physiological effects. Removal of unreacted and spent reducing agent may be conveniently and efficiently achieved using various chromatogaphic methods, e.g., Sephadex gel treatment, micropore filtration, centrifugation, etc. The particular manner of separation is not critical to the invention.

Depending upon the particular metal, various conditions and techniques will be employed for preparing the metal radionuclide species for labeling of the H-treated product. To prepare the technetium species, sodium pertechnetate is reacted in solution in the presence of a reducing agent, e.g., stannous ion or dithionite under conventional conditions. Desirably, a weak chelating agent is included in the medium such as tartrate, glucoheptonate, etc., whereby a labile, soluble complex of reduced Tc-99m is formed. Rhenium species for labeling may be formed by reducing perrhenate to rhenium (IV) hexachloride employing hypophosphorous acid in concentrated HCl at 95° C. The hexachlororhenate is then converted to the bis(ethylenediamine)dioxorhenium (V) in 90% ethylenediamine with oxygen at room temperature. The bis(ethylenediamine)dioxorhenium (V) complex is then recovered by evaporation or recrystallization, and the ethylenediamine removed under vacuum with heating. Radioactive copper species suitable for radiolabeling the selected H-treated product may be formed by dissolving copper oxide (CuO) in glacial acetic acid and evaporating the acetic acid to yield copper acetate, which may then be dissolved in water for radiolabeling.

Labile complexes of the metal radionuclide species may also be employed as a source of the radionuclide for complex formation with the H-treated product. For example, Tc-99m gluconate, glucoheptonate, tartrate, malonate, or the like may be used. Similarly, weakly chelated complexes of the radionuclides may be used, including, for example, bis(ethylenediamine)copper (II) chloride, bis(aquo)-ethylenediamino copper sulfate or nitrate, and the like.

Typically, the selected H-treated proteinaceous substance or product is radiolabeled with the selected metal radionuclide species by first dissolving the radionuclide in an amount sufficient to result in a suitable radiation dose level in a physiologically acceptable medium, e.g. water or a suitable buffer solution; the selected H-treated product in a suitable buffer is then added. Preferably, the reaction solution or buffer will have a pH in the range of about 5 to 10, and the reaction will be allowed to proceed for a suffficient time for all of the H-treated product to complex with the metal radionuclide species. Usually the time of reaction will be less than about six hours and more than about 30 minutes, with temperatures ranging from about 0° to about 60° C., more usually between about 25° C. and about 50° C.

The H-treated products may be stabilized in a variety of ways for storage until radiolabeling is necessary. For example, following treatment with the reducing agent, the H-treated product may be frozen in desalted solutions at below about −10° C., usually about −20° C. It will prove more convenient to freeze-dry or lyophilize the H-treated products according to known techniques for storage at ambient or reduced temperatures, conveniently in individual sterile vials. Most conveniently, the H-treated products are stabilized with either a labile, complexing metal ion or with a sulfhydryl group derivatizing reagent. The stabilized H-treated products will then be frozen for future use or, more preferably, freeze-dried or lyophilized for storage as sterile powders.

Typically, with metal ion stabilization of the H-treated product, immediately following completion of the reaction between the reducing agent and the selected proteinaceous substance, an aqueous or buffered solution of a stoichiometric excess of a relatively weakly binding metal ion will be added. Preferably, the metal ions used is zinc ion ($Zn^{2+}$), but other divalent or trivalent metal ions such as, for example, calcium ion, magnesium ion, and the like may find use. Various weakly bound anionic salts of the metal ion may be used. Suitable anions may include chloride, iodide, phosphate, glycinate, acetate, gluconate, malonate, and the like. The metal ion and counter-ions should be biologically acceptable; toxic metal ions may only be used if the stabilized H-treated product is treated, as with ion exchange resins, prior to radiolabeling and administration. Therefore, these ions are less useful as requiring an additional purification step. The metal ion stabilized H-treated products are radiolabeled with metal radionuclide species in typically the same manner as the radiolabeling of H-treated products. The stabilizing metal ion will be chosen for rapid exchange with the particular radionuclide species in use; the stabilizing metal ion will be chosen such that the metal radionuclide species binds more strongly to the H-treated product than does the stabilizing ion.

Alternatively, the H-treated product can be stabilized against inactivation due to recombination of the bis(sulfhydryl) moieties to disulfide linkages with sulfhydryl group derivatizing reagents. Preferably, the sulfhydryl derivatizing reagents are selected to react with the sulfhydryl groups formed on treatment with the reducing agent and to be removable for radiolabeling. However, for some metal radionuclide species, such as, for example, $^{67}Cu^{2+}$ ion, it may be possible to select the derivatizing reagent such that removal of the derivatized group prior to radiolabeling is unnecessary. Preferably, the sulfhydryl groups are derivatized using cyanate (OCN$^-$) ion; other possible derivatizing reagents are acetic anhydride, N-acetylimidazole, maleic anhydride, succinic anhydride, sulfite ion, trinitrobenzosulfonic acid, and the like.

Cyanate is useful as a reversible and specific modifying reagent for sulfhydryl groups of proteins (G. R. Stark, *J. Biol. Chem.* (1964) 239: 1411). Under slightly acidic conditions (about pH 6) KNCO reacts specifically with the protein sulfhydryl groups to form S-carbamylcysteine. Under these conditions reaction with amino and guanidinyl groups is minimal. The decomposition of the S-carbamyl protein to the starting sulfhydryl and cyanate is alkali-catalyzed and occurs readily at pH 8 and above. Thus, cyanate protected, DTT treated antibody can be "activated" by brief exposure to alkaline pH prior to labeling with radionuclide or the "activation" and radiolabeling may be carried out simultaneously at alkaline pH. For example, Tc-99m-tartrate labeling is carried out at pH 8–10 and the cyanate protected protein is added to the radiolabeling reaction without prior activation.

The subject radiolabeled products may be administered to the mammalian host by injection, intravenously, intraarterially, peritoneally, intratumorally, subcutaneously for entry into the lymphatic system or the like, depending upon the particular site at which the radionuclide is desired. Generally, the amount to be injected into a host will depend upon the size of the host, with about 1 to 3000 μCi/kg of host. For human hosts, the dosage will usually be about 10–50 mCi/70 kg host, more usually about 25–35 mCi/70 kg host. For lower mammals, e.g., mice, the dose will be about 25–100 μCi for biodistribution studies, while up to or greater than 1000 μCi for imaging studies. After administration of the radionuclide, depending upon its purpose, the host may be treated in various ways for detection or therapy.

The following examples are offered by way of illustration and not by way of limitation.

EXAMPLE 1

Preparation of DTT-Treated Proteinaceous Substances a. Preparation of DTT-Treated Monoclonal Antibody To a solution of 25 mg of mouse monoclonal antibody in 2.5 ml phosphate-buffered saline solution (PBS; 0.05M phosphate, 0.15M sodium chloride, pH 7.5) was added a relatively concentrated solution of DTT in PBS to a final DTT concentration of 1 mM. The resulting solution was stirred for 30 minutes at room temperature.

The entire reaction mixture was purified on Sephadex G-25, previously equilibrated with PBS (1.5 cm×5.0 cm plastic column, eluted with PBS); 1.2 ml fractions were collected. The fractions, now desalted, with an absorbance (280 nm) greater than 0.1 were combined, aliquoted into small vials and frozen immediately at −20° C. Analysis of the reaction mixture by HPLC (Example 8) indicated the presence of only monomeric antibody in the pooled fractions, and thus the absence of aggregation.

b. Preparation of DTT-Treated Human Serum Albumin

To 6.0 mg of human serum albumin (HSA) and 1.2 ml of phosphate-buffered saline solution (PBS; 0.05M (50 mM) sodium phosphate; 0.15M sodium chloride; pH 7.5), a relatively concentration solution of DTT was added to a final DTT concentration of 1 mM. After stirring for 15 minutes at room temperature, the reaction mixture was desalted by elution from a Sephadex G-25 column according to the procedure outlined in Example 1a. The protein-containing fractions are pooled, aliquoted into small vials, and frozen at −20° C.

Alternate procedures for storing DTT-treated proteinaceous substances are described below.

EXAMPLE 2

Radiolabeling of DTT-Treated Proteinaceous Substances a. Labeling of DTT-Treated Monoclonal Antibody With Tc-99m-Tartrate A solution of Tc-99m-tartrate was prepared by adding 1.1 ml of degassed distilled water containing 9% ethanol to 100 μg (ca. 0.43 μmol) SnCl$_2$, 75 mg (ca. 0.32 mmol) disodium tartrate, and 3.2 mCi sodium (Tc-99m) pertechnetate. This mixture was heated at 50° C. with a water bath for 15 minutes. After cooling, in a separate container, 100 μl of the Tc-99m-tartrate solution, 200 μl of 0.2M, pH 8.0 sodium phosphate buffer, and 100 μg of DTT-treated antibody prepared as in Example 1 and thawed immediately before use were mixed. The total volume of the solution was adjusted to 0.5 ml with an aqueous solution of 0.15M sodium chloride and incubated at 50° C. for 60 minutes. HPLC analysis (Example 8) of the resulting solution indicated the presence of monomeric antibody only indicaating that no aggregation was caused by the labeling procedure.

Analysis of the reaction products according to the procedure of Example 7 indicated that 84% of the Tc-99m was bound to the antibody. A similar experiment was conducted omitting the DTT treatment of the antibody; the analysis of the reaction products indicated that only 18% of the Tc-99m was bound to the antibody.

b. Labeling of DTT-Treated Antibody with Tc-99m Glucoheptonate

This experiment was performed using the Glucoscan ™ kit (New England Nuclear, Cambridge, MA). A Glucoscan ™ vial was reconstituted with 3 mCi of sodium (Tc-99m) pertechnetate and sufficient aqueous 0.15M sodium chloride solution to yield a final volume of 1.0 ml. The vial was held at room temperature for 15 minutes. Separately, 200 μl of 0.2M, pH 6.0 sodium phosphate buffer, 100 μl of the Tc-99m-glucoheptonate solution prepared above, and 100 μg of the DTT-treated antibody prepared as in Example 1 were mixed. The total volume was adjusted to 0.5 ml with 0.15M sodium chloride solution and incubated at 50° C. for 60 minutes. HPLC analysis indicated the presence of only monomeric antibody. Analysis of the reaction products according to the procedure of Example 7 demonstrated that 95% of the Tc-99m was bound to the antibody. Antibody not treated with DTT, but subjected to the same Tc-99m glucoheptonate labeling procedure resulted in binding of only 6% of the Tc-99m to the antibody.

c. Radiolabeling of DTT-Treated HSA

In a vial, 100 μl of the Tc-99m-tartrate solution, prepared according to Example 2a, was combined with 200

μl of 0.2M, pH 8.0 sodium phosphate buffer and 100 μg of DTT-treated HSA, prepared according to the procedure of Example 1b. The total volume of the solution was adjusted to 0.5 ml with an aqueous 0.15M sodium chloride solution and incubated at 50° C. for 60 minutes. Analysis of the reaction products according to the procedure of Example 7 demonstrated that 89% of the Tc-99m was bound to the HSA.

EXAMPLE 3

Stability of Radiolabeled DTT-Treated Antibody

DTT-treated antibody was prepared according to the method of Example 1 and labeled with Tc-99m tartrate according to the procedure of Example 2a. Analysis of the reaction products according to the procedure of Example 7 showed 95% of the Tc-99m was bound to the antibody by this procedure. Diethylenetriaminepentaacetic acid (DTPA) was added to the solution of labeled antibody to a final concentration of 2 mg/ml. DTPA, an effective chelator of technetium, was thus present in a large excess. After heating the resulting solution for 60 minutes at 50° C. in a water bath, analysis according to Example 7 showed that 97% of the originally bound Tc-99m remained bound following treatment with DTPA.

EXAMPLE 4

Preparation of DTT-Treated Antibody Stabilized With Zinc Ion (Zn-DTT-Treated Antibody)

a. Without Removal of Excess Zinc Ion

DTT-treated antibody was prepared according to the procedure of Example 1, except that the final preparation was not frozen. An aqueous solution of zinc chloride ($ZnCl_2$) was immediately added to the solution of DTT-treated antibody to yield a solution with a final zinc ion concentration of 0.1 mM. This solution was stored at room temperature until further use.

b. Removal of Excess Zinc Ion

The method of Example 1 was followed, except that an aqueous solution of zinc chloride was added to the original reactin mixture to a final zinc ion concentration of 0.1 mM. The resulting solution was desalted on a Sephadex G-25 column previously equilibrated with PBA. The fractions containing the antibody were stored at room temperature.

c. Control Antibody

The procedure of Example 4b was followed with the ommission of DTT in order to characterize the antibody treated only with zinc ion.

EXAMPLE 5

Radiolabeling of Antibodies Stabilized With Zinc Ion

Separate solutions of untreated antibody, DTT-treated antibody (Example 1), Zn-DTT-treated antibody (Example 4a), desalted Zn-DTT-treated antibody (Example 4b), and control antibody (Example 4c) were each radiolabeled with Tc-99m tartrate according to the procedure of Example 2a. This labeling procedure was carried out immediately upon the preparation of the individual solutions. A second series of radiolabeling experiments were performed after storage of each of the five solutions at room temperature for 24 hours. Each of the ten solutions was analyzed according to the procedure of Example 6 for the percentage of Tc-99m bound; the results are presented in Table I.

EXAMPLE 6

Analysis of Extent of Radiolabeling

Thin layer chromatography (TLC) was used to determine the extent of protein radiolabeling. Silica gel impregnated glass fiber sheets were obtained from Gelman Sciences Inc., Ann Arbor, Mich. and activated according to the manufacturer's instructions. A 2-5 μl aliquot of the radiolabeling reaction mixture was spotted and the TLC strip developed in 0.65M ammonium acetate, 25% methanol. The TLC strip was cut in half and each half counted ina well radioactivity counter calibrated for the appropriate radionuclide. The protein and hence protein bound radioactivity remains at the origin and the non-protein radioactivity migrates with the solvent front. The extent of protein radiolabeling was calculated using the formula:

$$\% \text{ protein bound} = \frac{\text{counts of origin}}{\text{counts at origin} + \text{counts at solvent front}} \times 100\%$$

TABLE I

| Radiolabeling Experiments Demonstrating Zinc Ion Stabilization | | |
|---|---|---|
| Antibody Solution | Percent Tc-99m Bound Post-Preparation | Percent Tc-99m Bound After 24 Hours |
| Untreated Antibody | 24 | 24 |
| DTT-Treated Antibody | 85 | 24 |
| Zn-DTT-Treated Antibody | 82 | 81 |
| Zn-DTT-Treated Antibody, Desalted | 83 | 83 |
| Zn-Treated Antibody | 9 | 9 |

From these results, several observations may be made. DTT treatment of the antibody greatly increases the extent of radiolabeling with Tc-99m. However, if the DTT-treated antibody solution is allowed to stand at room temperature for 24 hours, the extent of Tc-99m bound is no greater than that which is bound to the untreated antibody. This indicates, and supports the hypothesis, that the DTT treatment reduces disulfide linkages in the antibody to produce bis(sulfhydryl) moieties which, in turn, recombine to form the original disulfide linkage within about 24 hours at room temperature.

The efficiency of post-preparation radiolabeling of the zinc DTT-treated antibody is essentially the same as the efficiency of the labeling without $Zn^{2+}$ addition. However, the additional treatment with zinc ion effectively prevents oxidation of the sulfhydryl groups, thus stabilizing the DTT-treated antibody and facilitating the use of the methods and compositions of the present invention for radiolabeling when clinically desired. The radiolabeling efficiency is essentially the same, at the zinc ion concentrations used, whether or not the Zn-DTT-treated antibody is desalted to remove excess zinc ion. Treatment of antibodies with zinc ion without DTT treatment actually decreases the radiolabeling efficiency.

EXAMPLE 7

High Performance Liquid Chromatographic (HPLC) Analysis of Aggregation

Size exclusion HPLC was performed using a Toyo Soda TSK 3000 column, 7.5 mm×30 cm (available from Kratos, Inc., Ramsey, NJ). The column was eluted with 0.2M sodium phosphate pH 7.0 with 0.15M sodium chloride running at 1.0 ml/min. The column eluant was monitored by using both an in line UV detector and an in line radioactivity detector. The column was calibrated using appropriate protein molecular weight standards and the control was the protein under study before radiolabeling.

EXAMPLE 8

Derivatization of DTT-Treated Antbody with Cyanate Ion

DTT-treated antibody (25 mg) was prepared according to the method of Example 1 except that the reaction mixture was purified on Sephadex G-25, previously equilibrated with 0.05M sodium phosphate, 0.15M sodium chloride, pH 6.0. Immediately after the chromatography, 60 μl of a 5 mg/ml aqueous solution of potassium cyanate was added and the pH kept at 6.0 by the addition of 1M acetic acid. After 30 minutes the solution was desalted on Sephadex G-25, previously equilibrated with PBS. The fractions containing the protein were combined, concentrated to about 10 mg/ml and stored at 4° C. The cyanate protected antibody is labeled with Tc-99m-tartrate by the method of Example 2a.

EXAMPLE 9

Binding of the "H-Treated Product" Labeled with Tc-99m to Human FMX-Met II Tumor Cells The effects that DTT treatment and subsequent Tc-99m labeling have upon the antibody component to bind the antigen against which it is targeted was assessed by a cell binding assay. The assay was a variant of that described by T. Lindmo, et al., *J. of Immunol. Meth.* (1984) 72: 77–89. Radiolabeled 9.2.27 antimelanoma antibody was incubated for a period of two hours with a fixed concentration of the human FMX-Met II melanoma tumor cells predetermined to represent conditions of antigen excess. As a control for nonspecific binding of the radiolabeled antibody to the tumor cells, tumor cells were preincubated for at least one hour in the presence of a 200 fold excess of nonradiolabeled antibody of the same specificity. Following incubation of the target cells and radiolabeled antibody, the level of radioactivity was quantitated in a gamma well counter. Analysis of the 9.2.27 monoclonal antibody in this manner demonstrated antigen specific binding to target cells of about 76%, with a nonspecific binding component of less than 4%.

By using the compositions and methods of the subject invention, one can rapidly radiolabel proteinaceous substances containing, in their native states, disulfide linkages to provide radionuclide substituted reagents for use in vivo. The reagents can be provided in pure form and good yield. The radiolabeling can be efficiently performed using mild conditions under which the proteinaceous substances are neither denatured nor aggregated. Further, the reactive proteinaceous substances provided by the treatment with DTT can be stabilized for long term storage at ambient temperatures and can then be radiolabeled as needed shortly prior to administration. Thus, one can safely direct a radionuclide to a desired site where only low levels of radioactivity will be non-specifically directed and bound. The compositions and methods according to the invention, provide for stably radiolabeled proteinaceous compositions having physiological properties of interest, with minimization of the effects of the biological activity of the proteinaceous substances so labeled.

Although the foregoing invention has been described in some detail by way of illustration and example for purposes of clarity of understanding, it will be apparent to those skilled in the art that certain changes and modifications may be practiced. Therefore, the description and examples should not be construed as limiting the scope of the invention, which is delineated by the appended claims.

What is claimed is:

1. A method of preparing a metal radionuclide-labeled protein from a protein precursor having at least oe disulfide linkage, the method comprising:
    reacting said protein precursor with a disulfide reducing agent to form a dimercaptoprotein;
    reacting said dimercaptoprotein with a divalent or trivalent cation to yield a cation-derivatized protien; and
    combining said cation-derivatized protein with $^{99m}Tc$, $^{186}Re$, $^{188}Re$ or $^{67}Cu$ to form said metal radionuclide-labeled protein.

2. The method of claim 1 wherein said protein precursor is a monoclonal antibody polyclonal antibody or specific binding fragment thereof.

3. The method of claim1 wherein the reducing agent is dithiothreitol.

4. The method of claim 1 wherein the cation is zinc ion.

5. The method of claim 1 further comprising, after the second reacting step, the steps of lyophilizing the cation-derivatized protein and solubilizing the cation-derivatized protein in aqueous buffered medium prior to said combining step.

6. The method of claim 1 further comprising, after the first reacting step, the step of freeing said dimercaptoprotein of spent and unreacted reducing agent.

7. The method of claim 1 further comprising, after the second reacting step, the step of freeing said cation-derivatized protein of spent and unreacted reducing agent.

8. A method of preparing a metal radionuclide-labeled protein from a protein precursor having at least one disulfide linkage, the method comprising:
    reacting said protein precursor with a disulfide reducing agent to form a dimercaptoprotein;
    stabilizing said dmercaptoprotein against inactivation by reaction of the dimercaptoprotein with a derivatizing agent for mercapto groups, thereby producing a derivatized protein having regenerable mercapto groups;
    regenerating said mercapto groups, thereby forming a regenerated dimercaptoprotein; and
    combining said regenerated dimercaptoprotein with $^{99m}Tc$, $^{186}Re$, $^{188}Re$ or $^{67}Cu$ to form said metal radionuclide-labeled protein.

9. The method of claim 8 wherein the derivatizing agent is cyanate ion.

10. The method of claim 8 further comprising the step of lyophilizing the dimercaptoprotein.

11. A product made by the method of any one of claims 1, 2, 3, 4, 5, 6 and 7.

12. A method of preparing a storage-stable metal radionuclide complexing protein comprising
   reacting a disulfide-containing protein precursor with a disulfide reducing agent to form a dimercaptoprotein; and
   reacting said dimercaptoprotein with a divalent or trivalent cation to produce a derivatized product, or with a derivatizing agent for mercapto groups to produce a regenerable derivatized product.

13. The method of claim 12 wherein said protein precursor is a monoclonal antibody, polyclonal antibody or specific bonding fragment thereof.

14. The method of claim 12 wherein the reducing agent is dithiothreitol.

15. The method of claim 12 further comprising the step of lyophilizing the derivatized product or the regenerable derivatized product.

16. The method of claim 12 further comprising, after the first reacting step, the step of freeing said dimercaptoprotein of spent and unreacted reducing agent.

17. The method of claim 12 further comprising, after the second reacting step, the step of freeing said derivatized product or said regenerable derivatized product of spent and unreacted reducing agent.

18. A product made by the method of any one of claims 12, 13, 14, or 15.

19. A kit comprising a sterile package containing the product made by the method of any one of claims 12, 13, 14, or 15.

20. A method for direct technetium-99m labeling of a disulfide-containing protein, comprising:
   forming a labile, soluble complex of reduced technetium-99m;
   reacting said disulfide-containing protein with dithiothreitol to form a dimercaptoprotein; and
   combining said dimercaptoprotein with said labile, soluble complex of reduced technetium-99m in a reaction solution or buffer having a pH from about 5 to about 10.

21. The method of claim 20 wherein the protein is a monoclonal antibody, a polyclonal antibody or a specific binding fragment thereof.

22. A product made by the method of claim 20 or 21.

23. A method for directly labeling a storage-stable dimercaptoprotein with a metal radionuclide, comprising:
   reacting a disulfide-containing protein with a reducing agent to form a dimercaptoprotein;
   lyophilizing said dimercaptoprotein, thereby forming a storage-stable dimercaptoprotein;
   rehydrating said storage-stable dimercaptoprotein, thereby forming a regenerated dimercaptoprotein; and
   combining said regenerated dimercaptoprotein with $^{99m}$Tc, $^{186}$Re, $^{188}$Re or $^{67}$Cu to obtain said metal radionuclide-labeled protein.

24. The method of claim 23 wherein the protein is a monoclonal antibody, a polyclonal antibody or a specific binding fragment thereof.

25. The method of claim 23 wherein the reducing agent is dithiothreitol.

* * * * *

UNITED STATES PATENT AND TRADEMARK OFFICE
CERTIFICATE OF CORRECTION

PATENT NO. : 4,877,868

DATED : October 31, 1989

INVENTOR(S) : John M. Reno, Becky J. Bottino, D. Scott Wilbur

It is certified that error appears in the above-identified patent and that said Letters Patent is hereby corrected as shown below:

| | | |
|---|---|---|
| Column 2, | line 43: | "froma" is changed to --from a-- |
| Column 4, | line 42: | "ions" is changed to --ion-- |
| Column 4, | line 48: | "counter-ions" is changed to --counter-ion-- |
| Column 6, | line 2: | "concentration" is changed to --concentrated-- |
| Column 6, | line 5: | "froma" is changed to --from a-- |
| Column 6, | line 32: | "indicaating" is changed to --indicating-- |
| Column 7, | line 44: | "reactin" is changed to --reaction-- |
| Column 7, | line 52: | "ommission" is changed to --omission-- |
| Column 8, | line 14: | "ina" is changed to --in a-- |
| Column 9, | line 17: | "Antbody" is changed to --Antibody-- |
| Column 10, | line 7: | "of" is changed to --on-- |
| Column 10, | line 20: | "oe" is changed to --one-- |
| Column 10, | line 25: | "protien" is changed to --protein-- |

UNITED STATES PATENT AND TRADEMARK OFFICE
CERTIFICATE OF CORRECTION

PATENT NO. : 4,877,868

DATED : October 31, 1989

INVENTOR(S) : John M. Reno, Becky J. Bottino, D. Scott Wilbur

It is certified that error appears in the above-identified patent and that said Letters Patent is hereby corrected as shown below:

Column 10, line 30: "antibody" is changed to --antibody,--.

Column 10, line 54: "dmercaptoprotein" is changed to --dimercaptoprotein--.

Signed and Sealed this

Twenty-first Day of April, 1992

Attest:

HARRY F. MANBECK, JR.

Attesting Officer     Commissioner of Patents and Trademarks